(12) United States Patent
Levi et al.

(10) Patent No.: US 12,220,244 B2
(45) Date of Patent: Feb. 11, 2025

(54) SHORT WAVE INFRARED BEDSIDE OR INTRA OPERATIVE ASSESSMENT OF WOUND OR BURN DEPTH AT DRY-WET LAYERS AND READINESS FOR RECONSTRUCTION

(71) Applicant: THE REGENTS OF THE UNIVERSITY OF MICHIGAN, Ann Arbor, MI (US)

(72) Inventors: Benjamin Levi, Boston, MA (US); Omer Berenfeld, Ann Arbor, MI (US); Michael D. Morris, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 859 days.

(21) Appl. No.: 16/470,678

(22) PCT Filed: Dec. 21, 2017

(86) PCT No.: PCT/US2017/067856
§ 371 (c)(1),
(2) Date: Jun. 18, 2019

(87) PCT Pub. No.: WO2018/119209
PCT Pub. Date: Jun. 28, 2018

(65) Prior Publication Data
US 2019/0320969 A1  Oct. 24, 2019

Related U.S. Application Data

(60) Provisional application No. 62/437,072, filed on Dec. 21, 2016.

(51) Int. Cl.
*A61B 5/00* (2006.01)
*A61B 5/107* (2006.01)

(52) U.S. Cl.
CPC ............ *A61B 5/445* (2013.01); *A61B 5/0075* (2013.01); *A61B 5/0077* (2013.01);
(Continued)

(58) Field of Classification Search
CPC ..... A61B 5/445; A61B 5/0075; A61B 5/0077; A61B 5/1075; A61B 5/1079;
(Continued)

(56) References Cited

U.S. PATENT DOCUMENTS

2003/0139667 A1   7/2003   Hewko et al.
2006/0155193 A1   7/2006   Leonardi et al.
(Continued)

FOREIGN PATENT DOCUMENTS

WO   WO-2009131989 A2   10/2009

OTHER PUBLICATIONS

Wilson et al (Quantitative short-wave infrared multispectral imaging of in vivo tissue optical properties, Journal of Biomedical Optics, vol. 19, Issue 8, 086011, Aug. 2014). (Year: 2014).*
(Continued)

*Primary Examiner* — Serkan Akar
(74) *Attorney, Agent, or Firm* — Harness, Dickey & Pierce, P.L.C.

(57) ABSTRACT

A short wave infrared (SWIR) imaging system and method of using the same is provided for assessing a tissue damage depth and/or readiness for reconstruction and/or debridement. The SWIR imaging system includes a light source for illuminating the wound or burn, an image light-registering camera system having at least one narrow-band SWIR filter to image the wound or burn and output imaging information, and a detection system for receiving the imaging information and processing the imaging information to determine a tissue damage depth and/or readiness for reconstruction and/or debridement assessment.

7 Claims, 9 Drawing Sheets

(52) U.S. Cl.
CPC .......... *A61B 5/1075* (2013.01); *A61B 5/1079* (2013.01); *A61B 5/4878* (2013.01); *A61B 5/7203* (2013.01); *A61B 2503/40* (2013.01)

(58) Field of Classification Search
CPC . A61B 5/4878; A61B 5/7203; A61B 2503/40; A61B 5/444; A61B 5/00
See application file for complete search history.

(56) References Cited

U.S. PATENT DOCUMENTS

| | | | |
|---|---|---|---|
| 2014/0183362 A1* | 7/2014 | Islam | A61B 5/0022 250/338.4 |
| 2014/0188094 A1* | 7/2014 | Islam | A61B 18/203 606/7 |
| 2015/0011892 A1 | 1/2015 | Sostek | |
| 2016/0051147 A1 | 2/2016 | Cohen et al. | |
| 2016/0069743 A1* | 3/2016 | McQuilkin | G01N 21/255 356/416 |
| 2016/0327476 A1* | 11/2016 | Islam | A61B 5/4547 |
| 2016/0349228 A1* | 12/2016 | Kester | G01J 5/0014 |

OTHER PUBLICATIONS

Bashkatov et al_Optical properties of human skin, subcutaneous and mucous tissues in the wavelength range from 400 to 2000 nm; 2005 J. Phys. D: Appl. Phys. 38 2543.*
International Search Report and Written Opinion for PCT/US2017/067856, mailed Apr. 17, 2018; ISA/KR.

* cited by examiner

Burn Depth

SWIR Images

SWIR Reflectance Intensity

SHORT WAVE INFRARED BEDSIDE OR INTRA OPERATIVE ASSESSMENT OF WOUND OR BURN DEPTH AT DRY-WET LAYERS AND READINESS FOR RECONSTRUCTION

CROSS-REFERENCE TO RELATED APPLICATIONS

This application is a U.S. National Phase Application under 35 U.S.C. 371 of International Application No. PCT/US2017/067856 filed on Dec. 21, 2017. This application is based on and claims the benefit from U.S. Provisional Application No. 62/437,072, filed on Dec. 21, 2016. The entire disclosures of all of the above applications are incorporated herein by reference.

FIELD

The present disclosure relates to tissue moisture assessment and, more particularly, relates to bedside or intra-operative assessment of tissue damage depth and readiness for reconstruction and/or treatment.

BACKGROUND AND SUMMARY

This section provides background information related to the present disclosure which is not necessarily prior art. This section also provides a general summary of the disclosure, and is not a comprehensive disclosure of its full scope or all of its features.

Thermal injuries are a significant cause of morbidity and mortality in the United States. Given the lack of objective measures available to clearly differentiate superficial from deep partial thickness burns, patients undergo either disproportionately more or less surgery than what is appropriate 40% of the time, leading to longer hospital stays and poor outcomes. The present teachings provide a system and method for using short wave infrared (SWIR) imaging to differentiate superficial from deep burns based on variations in moisture level.

Thermal injuries represent a significant public health burden given that over 265,000 people die of burn injuries each year. In the United States alone, over 400,000 people receive medical care for burn injuries each year, with over 10% of these injuries requiring hospitalization and surgical intervention. A portion of the economic burden incurred in the management of these injuries stems from a lack of diagnostic tools available to guide clinicians in the effective and efficient management of these patients at the time of surgical intervention. The current standard of care relies on clinical judgment and clinician experience, factors that are difficult to appraise critically due to the absence of objective data and standardization. While guidelines exist to promote the practice of evidence-based medicine, such recommendations are difficult to implement without the proper technology designed to enhance clinician judgment and practice.

With regards to burn care specifically, the depth of injury dictates treatment outcomes. It is well known that while superficial and superficial partial thickness burns heal well without surgery, deep partial thickness injuries require prompt debridement and grafting to prevent adverse sequelae of scar contractures, infections, and delayed wound healing. Thus, the crux of decision-making for burn surgeons lies in determining whether or not surgical debridement is necessary.

Clinically, physical examination is the most commonly utilized method to evaluate depth of injury, given that objective measurements of tissue viability such as histology from tissue biopsy are not performed in real-time and are impractical, expensive, invasive, and subject to sampling errors. Additionally, tissue biopsy only provides information at the site of the biopsy. Importantly, data show that in practice clinician judgment regarding the need for intervention correlates with objective measures of tissue viability only 60% of the time. That means some undergo either disproportionately more or less surgery than what is appropriate 40% of the time, leading to longer hospital stays and worse outcomes. Thus, an objective, practical method of measuring the depth of tissue injury is critical to enhance currently available diagnostic modalities, and improve treatment outcomes.

While new technologies have recently been developed to address this deficit, these modalities have important limitations that restrict the potential for standardized clinical use. Laser Doppler Imaging (LDI) utilizes the speed and volume of blood flow at a site to determine tissue viability. While studies have demonstrated greater than 95% correlation between histology and LDI in terms of accuracy in the assessment of tissue viability, this method requires large instruments for use that are not portable and are very expensive. Most importantly, however, LDI is not recommended for use during the first 48 hours or after the initial 5 days of presentation, or in patients with other comorbidities, such as anemia, cellulitis, or vascular disease. Thus, clinical applicability is severely limited as a result of these restrictions.

Indocyanine green (ICG) videoangiography is another modality of macroimaging used to visualize the patency of vasculature within the deep dermis. Using this system, patients receive an intravenous injection of ICG. Tissues that are viable demonstrate high uptake of ICG, while tissues that are less viable demonstrate lower uptake visualized as lower fluorescence. The main limitation of this modality is the need for intravascular injection, an invasive procedure that can result in pain, anaphylaxis, headache, and urticaria. Near infrared imaging (NIR) has been previously used to assess burn wound edema, however, translation of this technology to the clinical setting has not yet occurred. It has been reported that NIR is only able to consistently assess deeper tissues for edema. This confounded reported results as deeper burn wounds sometimes had increased deep cellular edema despite the fact that the surface was completely dry. Furthermore, NIR was not able to reliably and reproducibly assess levels of surface moisture, which is the primary region of interest with the SWIR system. Finally, extremity burn debridements are often done under tourniquet control thus preventing the use of NIR or LDI given that they rely on blood flow.

Therefore, better methods of imaging to evaluate tissue viability and guide the need for surgical debridement are necessary. Short wave infrared spectroscopy (SWIR) is a viable and reliable solution. Because light in the SWIR range accurately detects moisture levels, the use of, for example, a 1940 nm wavelength represents a significant advancement in technology applicable to wound care. In fact, the absorption of water is 260-fold greater at SWIR of 1940 nm than at NIR of 970 nm (FIG. 1A), a factor relevant to wound care, because healing is enhanced in the presence of moisture.

Therefore, according to the teachings of the present invention, a system and method using short wave infrared (SWIR) imaging to differentiate superficial from deep burns based on variations in moisture level is provided. The system is validated herein using an inert compound, a mouse model in vivo, and ultimately in a validated porcine thermal injury model. It was determined that the imaging device of the present teachings can delineate moisture penetration at different depths within tissues, making it ideal for use burn injuries or other tissue issues. Employment of this technology will allow for improved pre- and intraoperative surgical guidance for burn surgeons in a point of care fashion in real time.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3A:
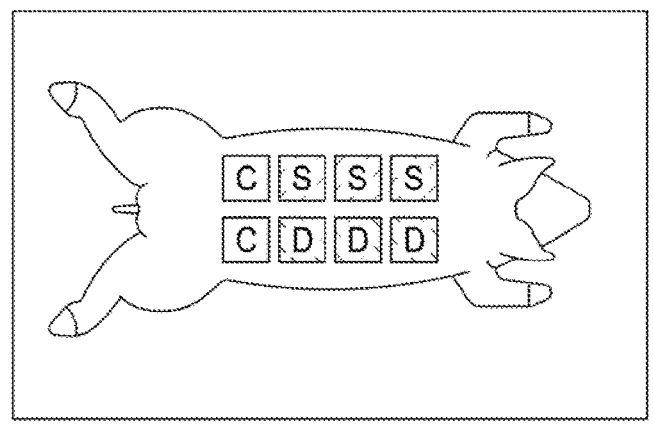
FIG. 3A illustrates the validated porcine thermal injury model, three superficial partial thickness (upper row) and three deep partial thickness (lower row) wounds were created at the same time and followed for 48 hours. After 48 hours, SWIR images were taken for each burn site.
Figure 3A:
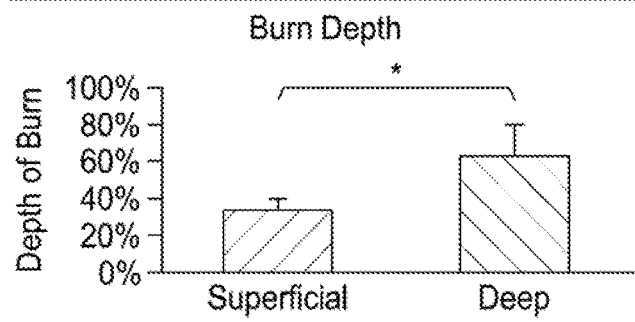
Figure 3B:
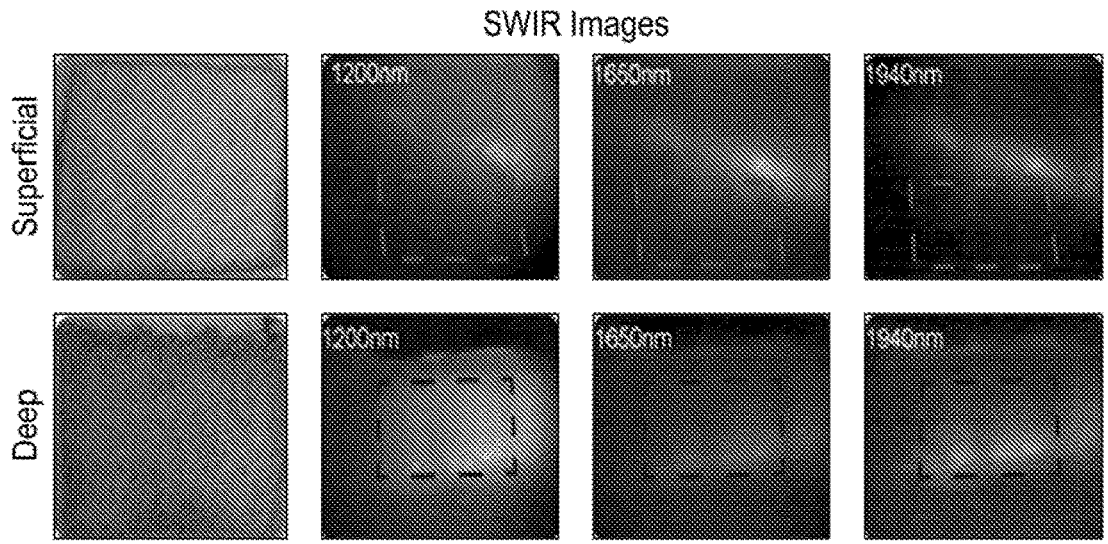
Figure 3B:
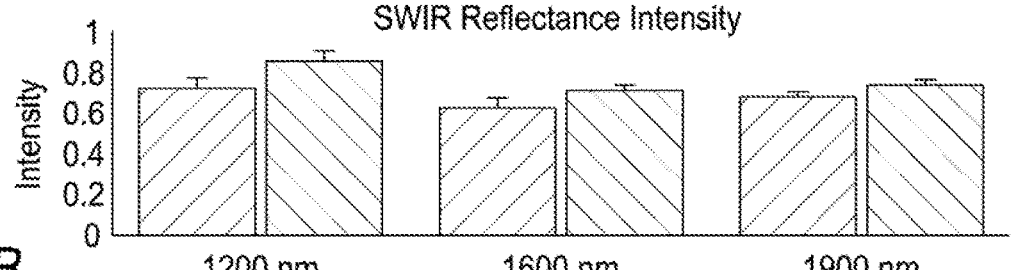

FIG. 3B is representative images of burns in the visible (left panels) and SWIR spectra at 1200 nm (second column panels), 1650 nm (third column panels), and 1940 nm (fourth column panels), which show little attenuation of reflectance signals within the area of the deep burn site (blue frame, dry) and highly attenuated reflectance signal in the surrounding normal (moist) skin. Overall, the superficial burn sites (upper row dashed areas) show more attenuation in reflected SWIR light as compared to deep burn sites (lower row dashed areas).

Figure 3C:
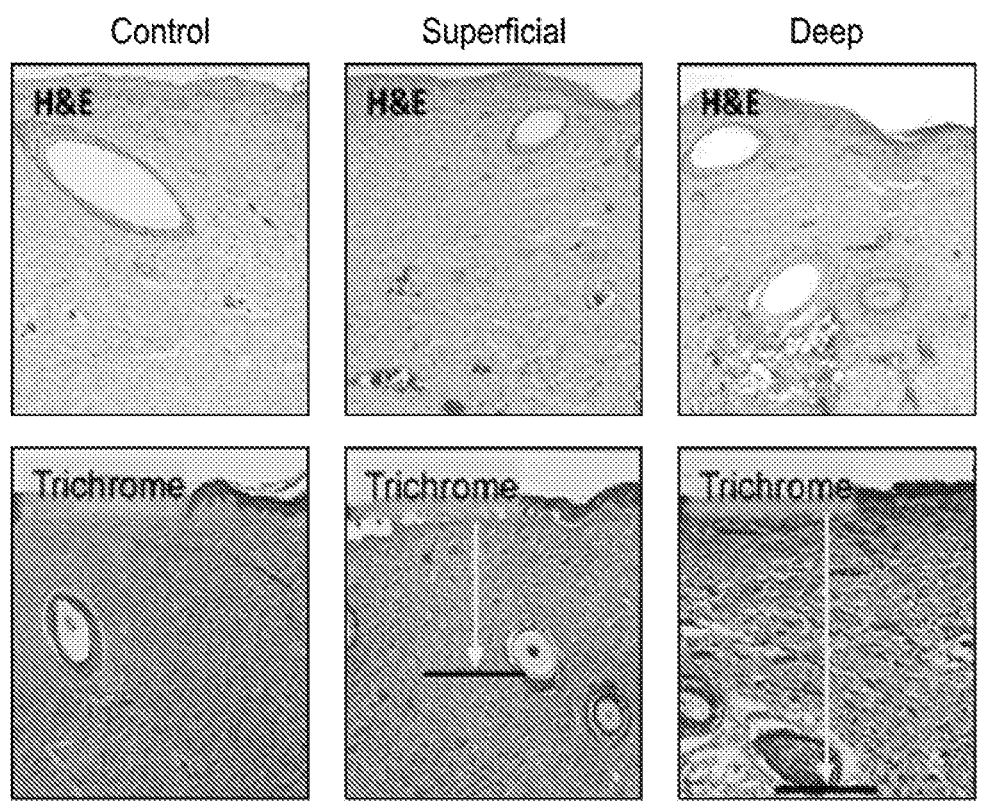

FIG. 3C illustrates histology taken at 48 hours with H&E and trichrome stains was used to confirm burn depth in accordance with the gold standard by measuring the depth of injury from epidermis to the deepest site of collagen coagulation, vascular or adnexal injury. Average depth of injury in superficial partial thickness burns was 32% and 64% for deep burns (p=0.0002). Additional, morphological features noted on H&E staining including epidermal erosion, lymphocytic invasion, and nuclear blurring support the diagnosis.

Figure 3D:
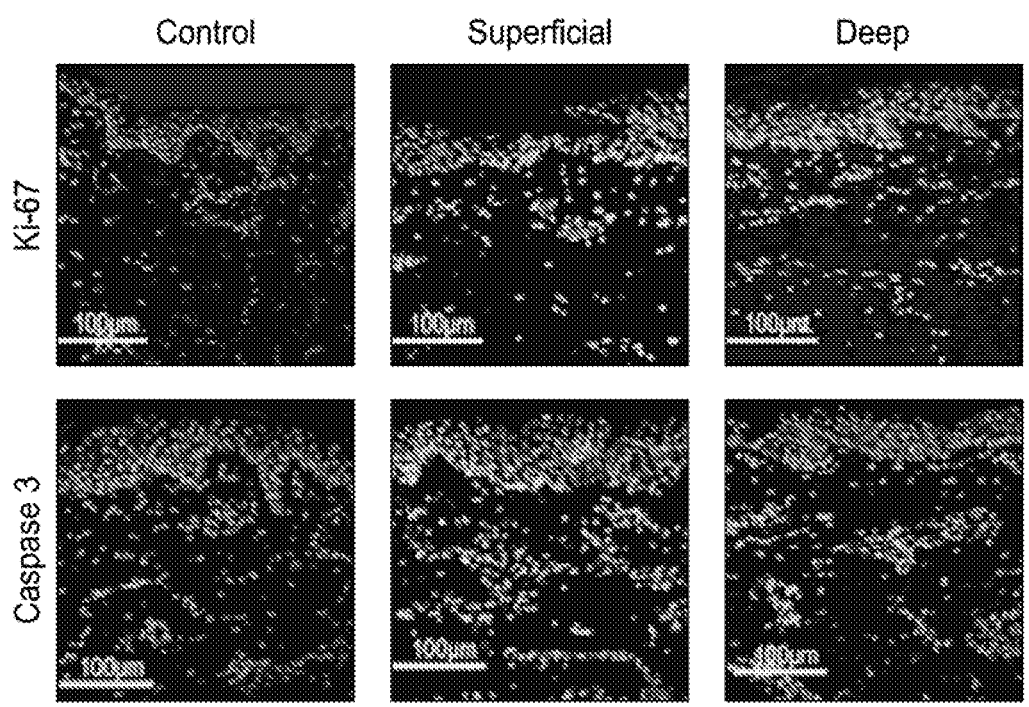

FIG. 3D illustrates immunofluorescence for a proliferative marker, Ki-67, is increased from the control in the superficial partial thickness burn and absent in the deep, suggesting that the superficial burn sites were more viable and may be better managed with conservative treatment. The apoptotic marker, Caspase 3, was increased most in the deep partial thickness injury, greater than in the superficial injuries suggesting that the tissue may benefit from early excision.

Figure 4A:
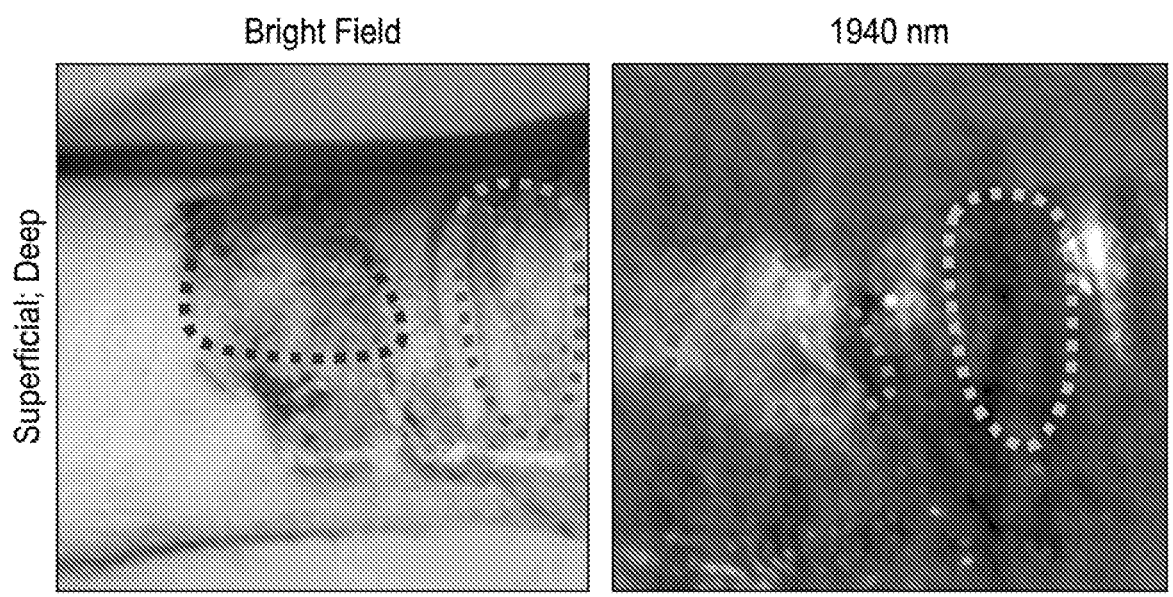

FIG. 4A illustrates a bright field and SWIR image at 1940 nm of human hand burn with unburned and superficial burns (right side box), and full thickness burn (left side box). Deeper burns appear lighter with the camera (less moisture and less attenuation of reflected light) validating its ability to stratify human burn wounds.

Figure 4B:
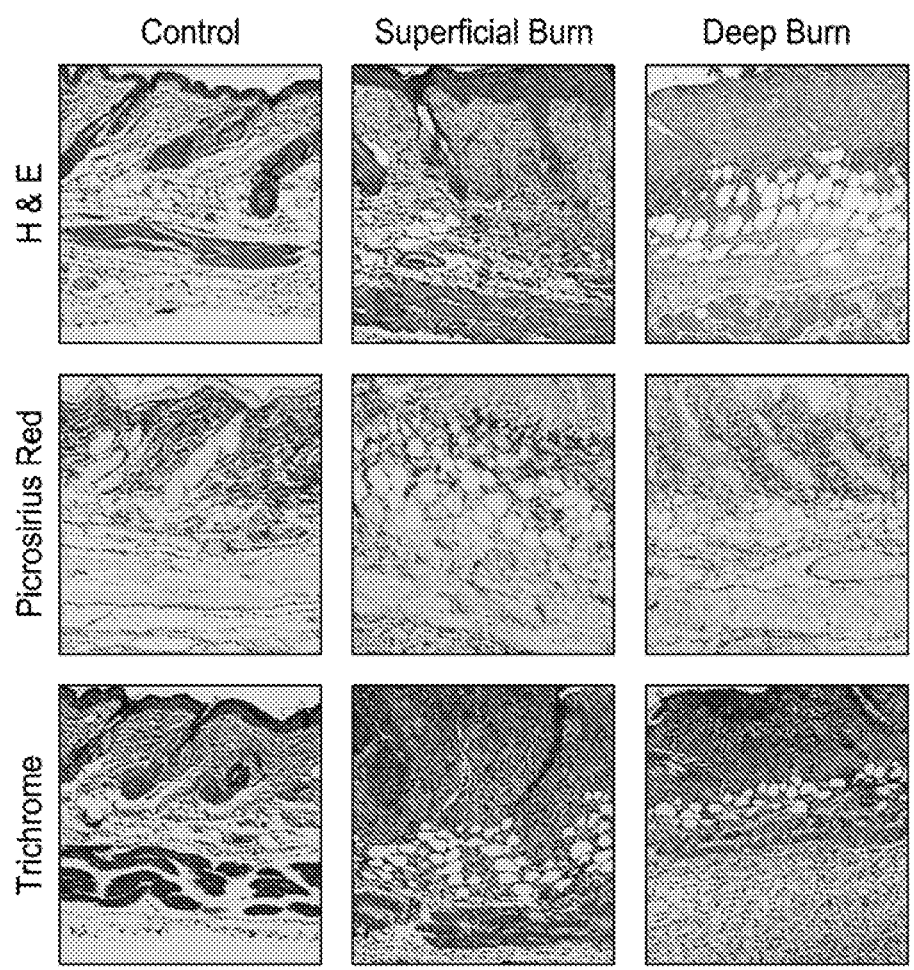

FIG. 4B illustrates that these findings correlate with the depth of injury as depicted by H&E stain. Superficial burns are defined by minimal injury to the dermis. Deeper burns are defined by significant damage to both the dermis and epidermis. These values also correlate with SWIR findings ($p<0.05$).

Figure 5:
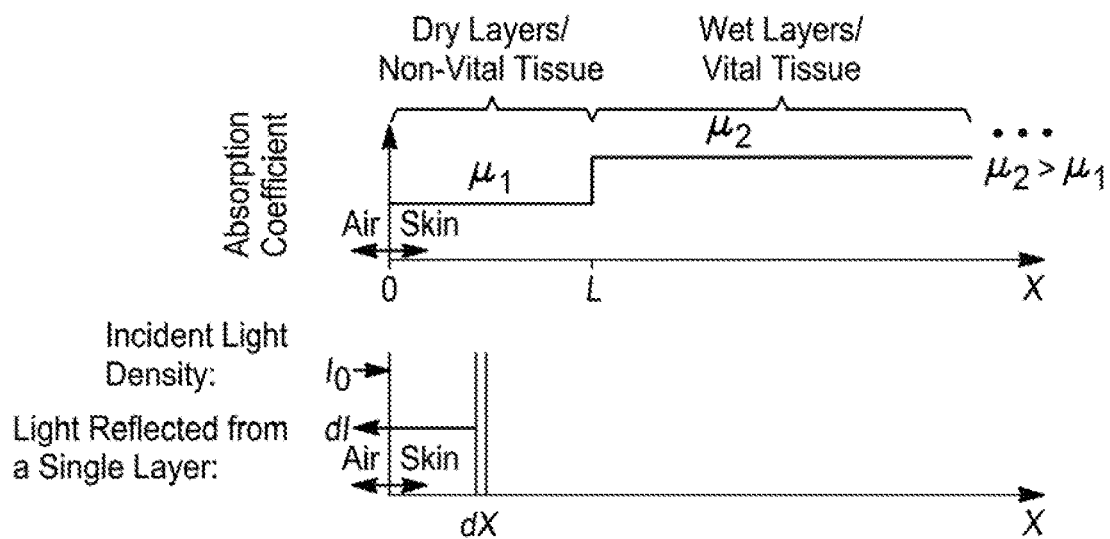

FIG. 5 is an illustration of skin and light models. The top illustrates absorption coefficients versus the distance from the air-skin interface (depth). L indicates the depth of transition between dry ($\mu_1$) and wet ($\mu_2$) tissue. The bottom is a diagram showing a light beam with intensity density $l_0$ is incident on the skin (right pointing arrow) and is reflecting an intensity dl from an internal layer thickness dX (left pointing arrow). The total reflected light intensity is the integration of the light reflected at all layers between zero and infinity.

Figure 6:
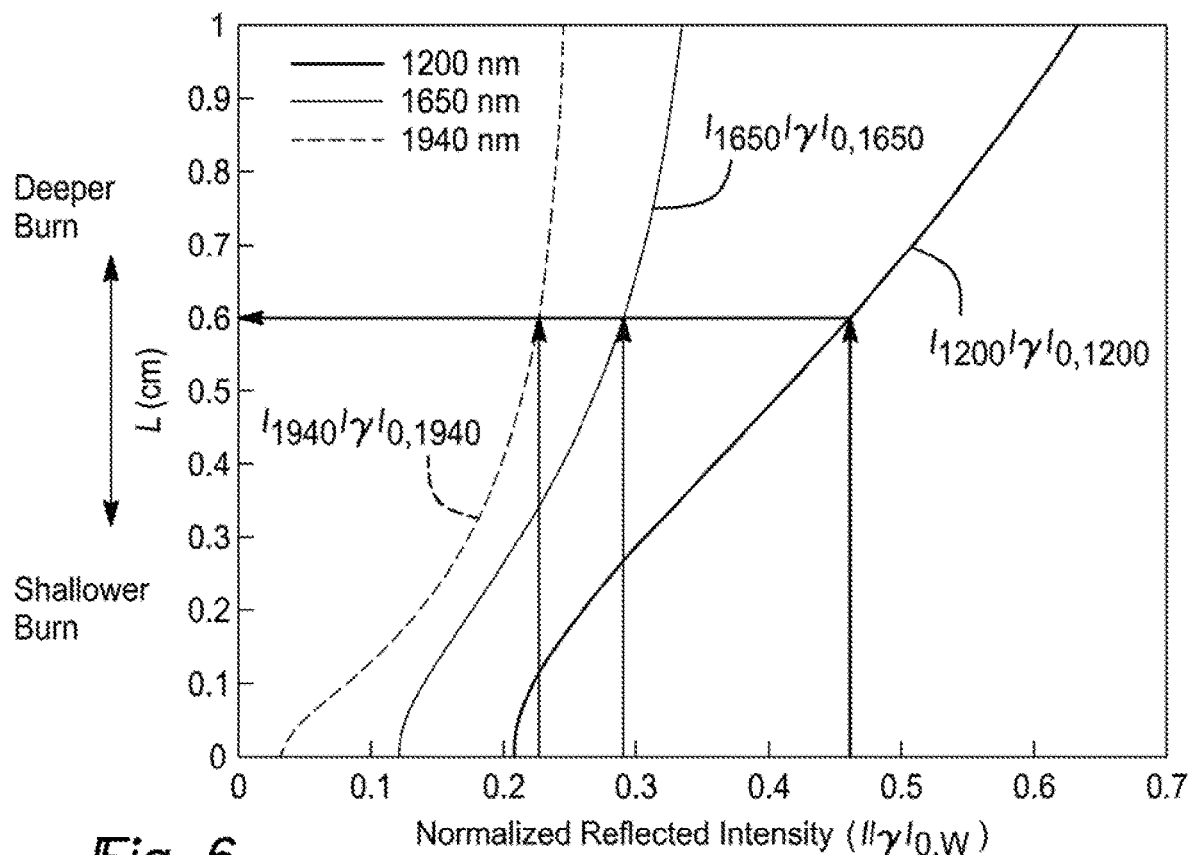

FIG. 6 is a graph showing traces of depth of burn (L) as a function of the reflected light intensity (I) normalized by the scattering factor γ and the incidence light for each different wavelength $I_{0,w}$ (w=1200, 1650, 1940 nm) based on Equation 1.

Figure 7:
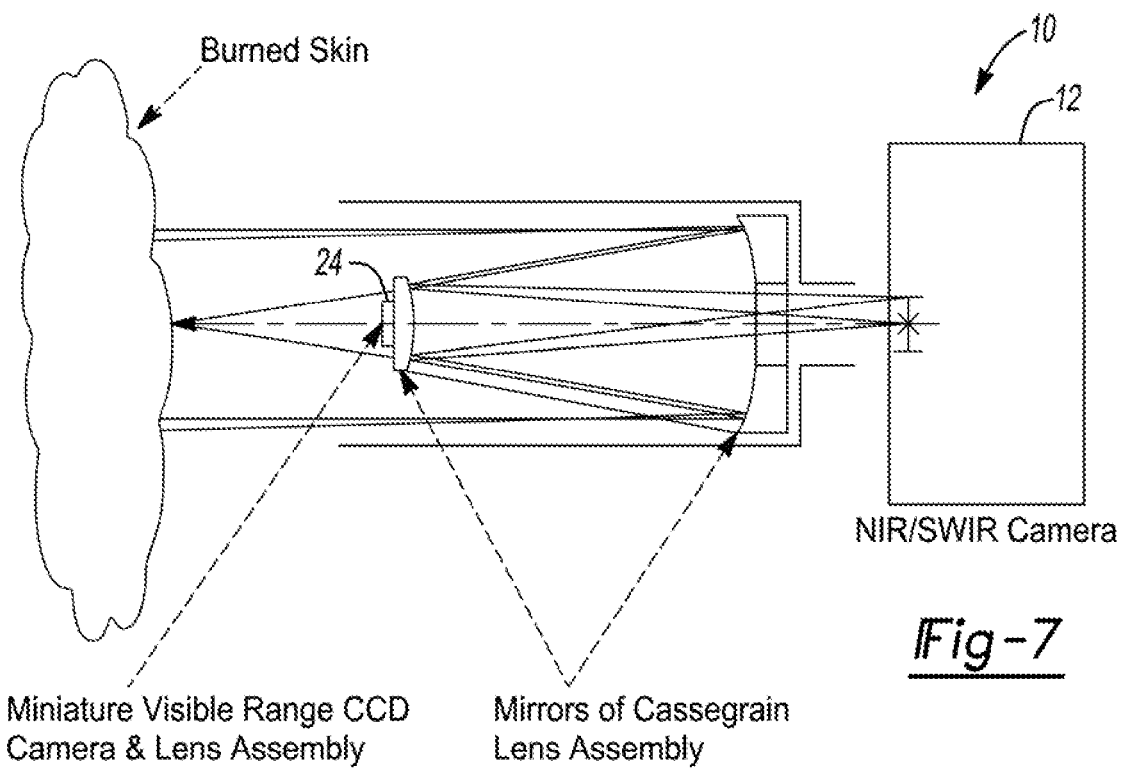

FIG. 7 illustrates the visible light CCD camera attached to the front Cassegrain mirror on the same optical axis of the SWIR camera 12 behind the rear mirror. A double-focal objective lenses assembly will be placed between the imaging device and the skin to create a focused image of both cameras simultaneously.

Figure 8:
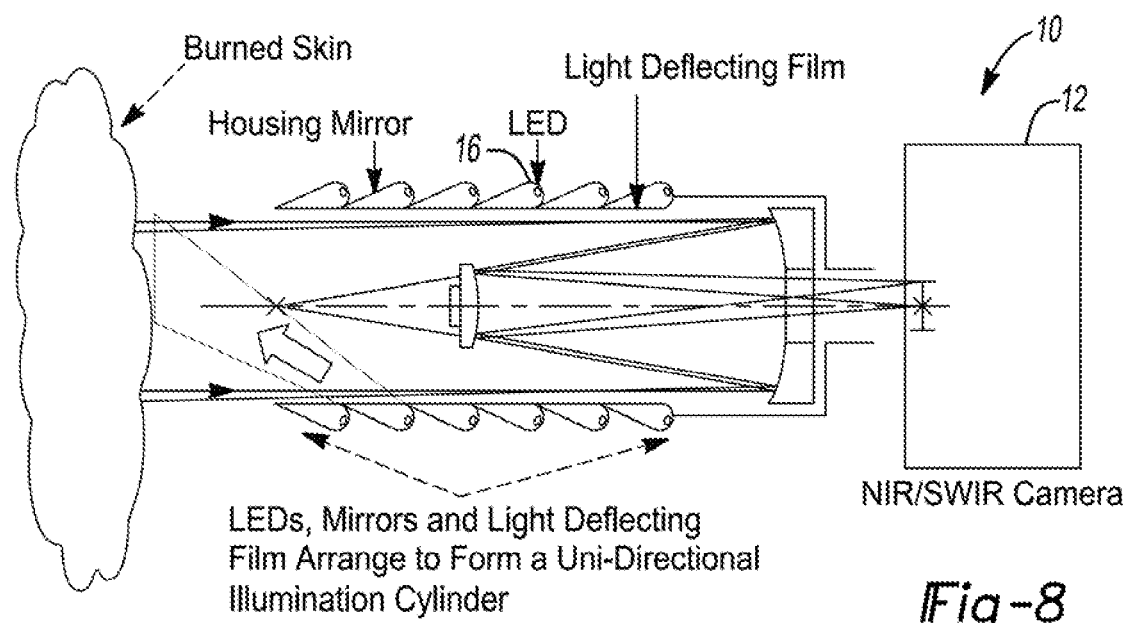

FIG. 8 is a diagram of a uni-directional light source that is best fit to match the Cassegrain imaging set up shown in FIG. 7.

Figure 9:
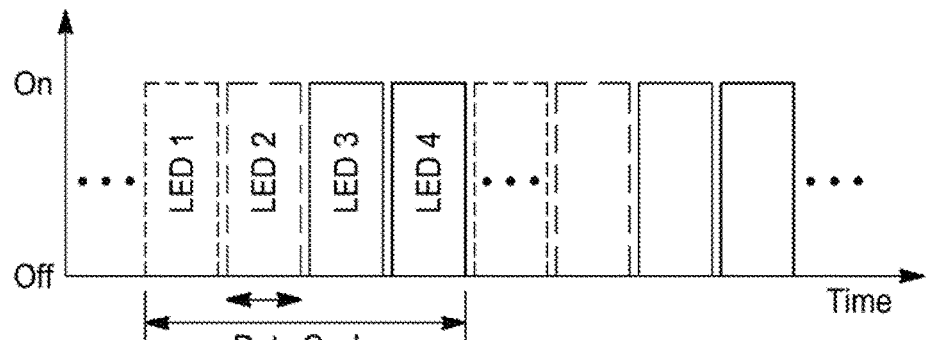

FIG. 9 illustrates time-course protocol for multi-spectral light sources protocol. Each LED type is powered in sequence for 1/350 sec (short arrows) to complete a duty cycle (long arrow) that can be repeated.

Figures 10A, 10B, 10C:
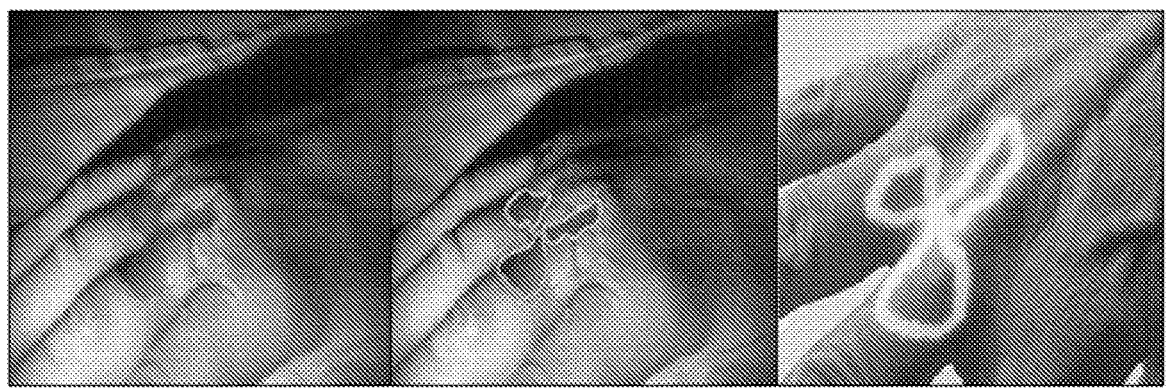

FIG. 10A illustrates a computer imaging display including the SWIR image.

FIG. 10B illustrates a computer imaging display including the burn boundary superimposed on the SWIR image.

FIG. 10C illustrates a computer imaging display including the visible light image and or on the visible light image.

Figure 11:
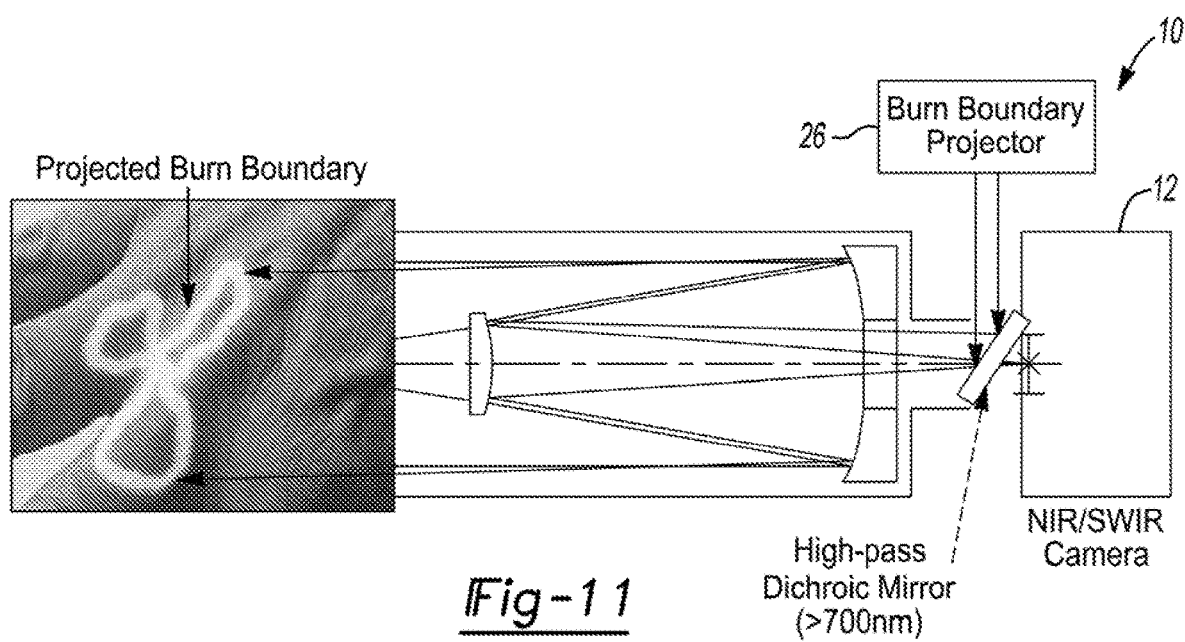

FIG. 11 illustrates projection of the burn boundary directly upon a treatment site. Other information, such as areas of interest or special markers, can also be projected on the skin.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, a short wave infrared (SWIR) imaging system to differentiate superficial from deep burns based on variations in moisture level is provided. The SWIR imaging system of the present teachings can delineate moisture penetration at different depths within tissues, making it ideal for use with burn injuries or tissue damage. Although the present teachings will be discussed in detail in connection with burn and wound treatment, it should be understood that the principles of the present teachings are not limited thereto and are equally applicable for any treatment, analysis, and/or imaging of burns, sores (e.g. pressure sores), wounds (e.g. thermal wounds, diabetic wounds, etc.), ulcers (e.g. Venus stasis ulcers), and other tissue damage phenomenon. The scope of the claims should not be regarded as being limited unless otherwise specifically claimed. Development of this technology will allow improved pre- and intraoperative surgical guidance for burn surgeons in a point of care fashion in real-time.

Moreover, according to the principles of the present teachings, a non-invasive point of care short wave infrared (SWIR) spectroscopic imaging system enables clinicians to more clearly diagnose superficial versus deep partial thickness burns based on surface moisture with tissue viability as the key variable of interest thereby guiding their treatment toward excision or conservation. This device, like a conventional point and shoot camera, does not contact the tissue and does not require the injection of fluorescent markers. It also does not require long acquisition times associated with other modalities.

The present teachings allow continuous imaging enabling uninterrupted feedback during a debridement when trying to determine when to halt debridement (when non-viable tissue is completely removed). Since no injection is used, the image does not become saturated as seen with the NIR imaging approach after a few injections. The development of a novel, accurate, non-contact, rapid, and portable point of care technology for use in military, veteran, and civilian treatment will allow a more objective assessment of burn wound depth. Importantly, SWIR imaging according to the present teachings remains accurate during tourniquet control because it does not depend on vascularity.

The present teachings will be discussed in connection with validating specific systems and procedures.

To this end, first, wide-field optical measurements of paper with varying degrees of moisture (0, 10, 20, 30 microliters of water) on the surface were quantified using a SWIR system 10 having a SWIR camera 12 (Xeva-2.35-320, Xenics, Leuven Belgium) with type 2 strained layer sensor 14 and collimated tungsten-filament light source 16 designed for uniform and angle-independent illumination, as illustrated, for example, in FIGS. 7, 8, and 11. It should be understood that alternative light sources 16 can be used, such as, but not limited to, tunable light source, tunable laser, laser, and the like. Briefly, the SWIR camera 12 at wavelengths of 1200 nm, 1650 nm, and 1940 nm was held approximately ten centimeters away from the object to provide uniform illumination prior to capture of the image. The images were processed using the Xenics software. The SWIR system 10 was validated to detect differences in water content on the surface of normal skin using a mouse model. Briefly, varying levels of moisture using water were applied to the dorsum of a mouse. The SWIR camera 12 (1200, 1650 and 1940 nm filters) was then used to image the site to ensure that moisture would be detectable using an in vivo model and live imaging.

Next, the ability of the SWIR system 10 to detect differences in water content within differing levels of burn injuries using a proven porcine burn model was employed. Briefly, superficial or deep burns were created on the dorsum of a pig (n=3/group). Non-adjacent, unburned tissue was used as a normal control. Each of the sites (burned and non-burned) was imaged using both a visible light camera followed by a SWIR camera 12 (1200, 1650 and 1940 nm filters). After imaging, the pig was euthanized and the skin was collected for histologic analysis, which served as the gold standard for tissue viability. Tissues were stained using hematoxylin and eosin (H&E) and Masson's trichrome. Immunofluorescence imaging was performed with Ki-67 to evaluate cell proliferation and caspase-3 as a marker of apoptosis.

Mouse Model

To evaluate the ability of SWIR system 10 to detect levels of moisture in vivo, varying levels of moisture were applied to the dorsum of a mouse (C57BL/6 male mouse; Charles River (Wilmington, MA)) at 6 weeks of age. The mouse was anesthetized using inhaled 1-3% isofluorane and euthanized upon completion of the procedure. SWIR imaging was next performed using 1200, 1650, and 1940 nm filters as described below.

Porcine Burn Model

One Yorkshire pig (Midwest Research Swine, Gibbon, MN) weighing 25 kg was singly housed with access to water and enrichment diet and allowed to acclimate to the facilities for at least 7 days prior to the procedures. Prior to the burn injury, the pig was pre-medicated with transdermal buprenorphine, 5 μg/hour (Butrans, Purdue Pharma, Stamford, CT). On the day of procedure, the pig was sedated with telazol (2.0-8.0 mg/kg IM) and xylazine (1.0-3.0 mg/kg IM). Anesthesia was maintained using 1-4% isoflurane in 100% oxygen delivered by mask. During the following two days, animal was briefly sedated with 1-3% isoflurane to facilitate image acquisition.

After induction of anesthesia, the animal's dorsal skin was prepped by chemically removing all hair with Nair (Church and Dwight, Ewing, NJ) for 15 minutes followed by a wash with warm water. The skin was then disinfected with chlorhexidine. Using a 5×5 cm, 150 g aluminum bar heated in a hot water bath (80° C.), three superficial burns were created by applying the block to the dorsum of the pig for 20 seconds. The same block was used to create the deep burns by increasing the time of application of the heated block to 60 seconds. The burns were adequately separated from one another to ensure complete isolation from the adjacent zones of thermal injury. The burn sites bandaged with Telfa™ (Medline, Mundelein, Ill.) and Tegaderm™(3M, St Paul, MN). The pig was then wrapped loosely with Coban™ (3M, St Paul, MN) from thorax to abdomen and a cotton jacket. Dressings were changed every 2 days. Full thickness punch biopsies (4 mm) were taken at the time of image acquisition.

Short Wave Infrared Imaging (SWIR) System

SWIR imaging was performed 24 hours after the burn was created. According to the principles of the present teachings, SWIR system 10 can comprise SWIR camera 12, such as a CCD camera (Xeva-2.35-320, Xenics, Leuven Belgium), equipped with one or more narrow-band SWIR filters, such as filters for 1200 nm, 1650 nm, and 1940 nm (+/−10 nm); a light source 16, such as a 400 Watt, 1600 lumen tungsten-filament light source and an optional dichroic mirror 20. All or a portion of SWIR system 10, such as SWIR camera 12, light source 16, filters, dichroic mirror 20, can be affixed to a mobile dolly, which ensured a constant angle between SWIR camera 12 and incident light from light source 16. Images were collected as 100 frame videos, uncompressed, 16-bit resolution and 10 frames per second. Each burn site was imaged individually along with 2 control regions of identical size on an uninjured area of nearby skin, from an approximate distance of 10 cm.

Image Processing

A sheet of white copy paper was imaged as a white balance and to create a de-noising mask as well as to normalize signal attenuation along the curvature of the pig dorsum. The 100 frames were averaged, and the light reflectance at the different wavelengths was used to generate a mask to normalize the image across the entire sampled regions of interest (ROI) drawn to correspond to the boundaries of each thermal injury site.

Histological Analysis

Full thickness punch biopsies (4 mm) were acquired 24 hours after the injury at the time of image acquisition. The tissue specimens were fixed in 10% buffered formalin for 24 hours at 4° C. and dehydrated in serial preparations of ethanol. In order to accurately diagnose the deep and superficial burns, the specimens were embedded in paraffin (Leica EG1150 C), cut into 5 μm sections longitudinally (Leica RM2255). Sections were then deparaffinized, rehydrated, and stained with Hematoxylin and Eosin (H and E) stain and Masson's Trichrome (Masson Kit, Sigma Aldrich®, St. Louis, Mo.). Depth of injury was determined within these specimens by measuring the length from the epidermis to the level of the deepest area of collagen coagulation, vascular insult, or adnexal injury using serially stained sections.

Immunofluorescent staining was performed for Ki-67 (ab16667, Abcam, Cambridge, Mass.) and Caspase-3 (1/1000, 9661, Cell Signaling, Danvers, Mass.). Five percent bovine serum albumin (BSA) in PBS and donkey serum was used to block specimens before appropriate secondary antibodies with attached fluorophores were applied. The specimens were then stained with DAPI and imaged for a red signal, signifying Ki-67 and caspase-3 positive staining.

Statistical Analysis

All statistical analyses were conducted after consultation with the Biostatistics Department at the University of Michigan. Statistically significant differences were considered at *$p<0.05$ for each method employed. A correlation coefficient was calculated to determine the ability of SWIR system 10 to predict tissue viability compared to histology as the gold standard. Parametric data was analyzed by ANOVA and Tukey-Fisher LSD criterion based on post-hoc t statistics. Non-parametric data was evaluated by Mann-Whitney testing, and the Kruskal-Wallis one-way analysis with Dunn's method in pairwise comparison. Intensity values of pixels within the ROI were normalized and histograms were made within the SciPy toolbox in iPython Notebook. Mixed Gaussian model analysis was performed to assess heterogeneity within the collected data from the SWIR system 10. Mean depth measurements for superficial and deep histological sections were compared via a 1-sided t test.

Results

Light in the SWIR region delineates differences in moisture content.

Figure 2A:
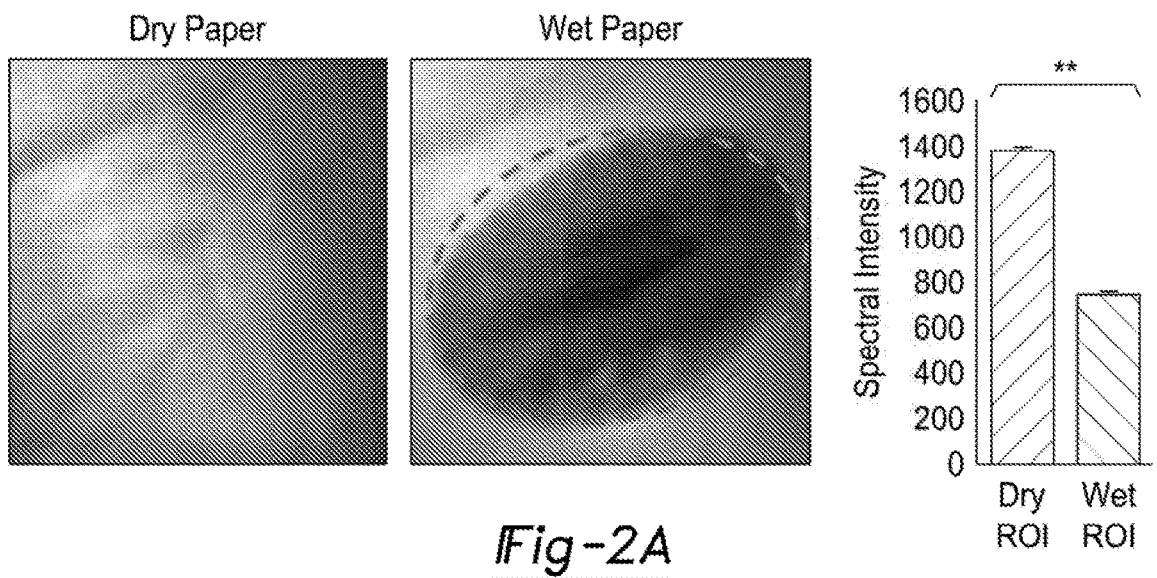
FIG. 2A illustrates the evaluation of the utility of the SWIR camera in the detection of water absorbance, an inert substrate (white copy paper) was wetted with 30 μL and imaged with a 1940 nm SWIR filter on a Xenics Xeva-2.35-320 camera under collimated tungsten-filament illumination. Significant signal attenuation is present under the wetted region highlighted in dashed line.
Figure 2B:
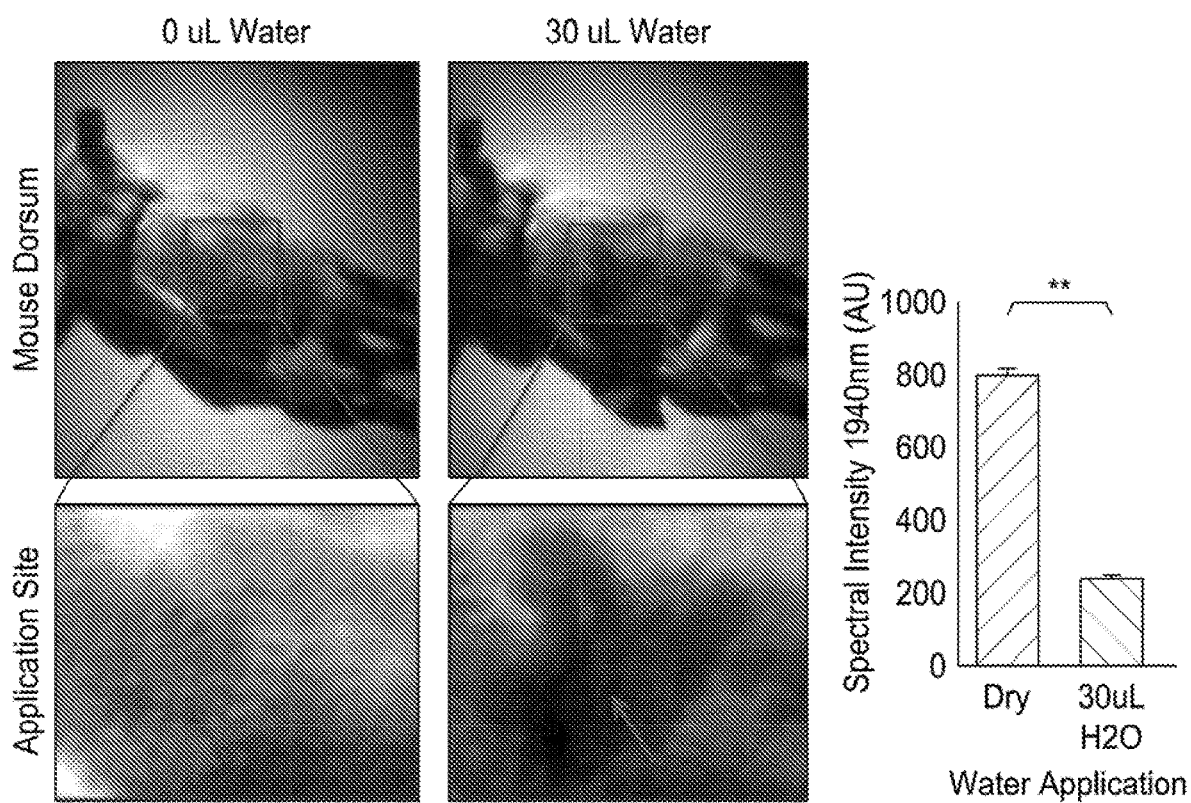
FIG. 2B illustrates SWIR images of mouse skin under normal conditions and after administration of 30 μL of water illustrates a similar pattern as with the paper, with a clear demarcation between skin that has been allowed to absorb the water and skin that was not exposed.

The ability of our SWIR system 10 to detect moisture in an inert compound was first demonstrated. It was found that reflectance intensity at the 1940 nm wavelength was significantly less in wet paper compared to dry paper (FIG. 2A). Additionally, the gradations of paper moisture can be seen with the central more densely moist region, demonstrating greater absorbance than the outer edge of the less moist paper. Next, the ability of this technology to delineate tissue moisture in a mouse model in vivo was validated (FIG. 2B), and similarly demonstrated a decrease in spectral intensity on moist skin compared to dry skin. Importantly, preliminary data suggests that light reflectance at 1940 nm is sensitive to water content. Based on the reflectance intensity, the hydrated mouse dorsum has an attenuated reflectance, compared to a dry surface at the same region. Given that deep partial thickness burns extend down to and include the apocrine and sebaceous glands, hair follicles and vasculature that regulate dermal hydration, these differences will likely translate into differences in moisture content between deep and superficial burns. Additionally, viable cells predominantly consist of water whereas burned cells or eschar are dry due to cell necrosis.

Light in the SWIR region differentiates tissue viability as a factor of burn severity and depth in a porcine burn model.

Porcine skin is a standard medical research model for human skin. A pig burn model was thus used to validate the ability of SWIR system 10 to distinguish partial from full thickness burns. Visible differences were evident in the superficial versus deep partial thickness injured sites along the dorsum of the pig (FIGS. 3A and 3B). The superficial and deep partial-thickness porcine injuries were validated with H&E and trichrome measuring the percent of injury as a function of total epidermal+dermal depth (FIGS. 3C and 3D). Mean values for 3 samples were 32% for superficial and 64% for deep partial thickness injuries (p=0.0002). These differences correlated with differences between superficial and deep partial thickness injuries as measured on the SWIR imaging system, confirmation that this technology is viable for use in routine clinical practice to differentiate superficial from deep partial thickness injuries. H&E and trichrome staining verified the differences in epidermal and dermal viability between tissues of the two groups seen by the SWIR system 10. Additionally, Ki67 staining demonstrates significantly diminished cellular proliferation within the deep burn compared to the superficial burn (FIG. 3D). Caspase-3 staining shows greater signal in the deep-dermal sections than in superficial, indicating decreased viability.

SWIR imaging correlates with histology and can detect differences in moisture level in tissue undergoing evaluation of superficial and deep partial thickness burns.

Figure 1A:
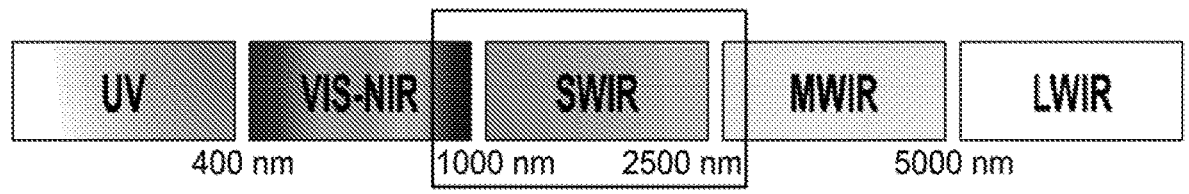
FIG. 1A illustrates that SWIR, defined here as wavelengths between 1000 nm and 2500 nm, lies in the wavelength region between visible-near infrared (VIS-NIR) and Medium Wave Infrared (MWIR) wavelengths, and encompasses 1940 nm, one of the most specific wavelengths for water spectroscopy.
Figure 1B:
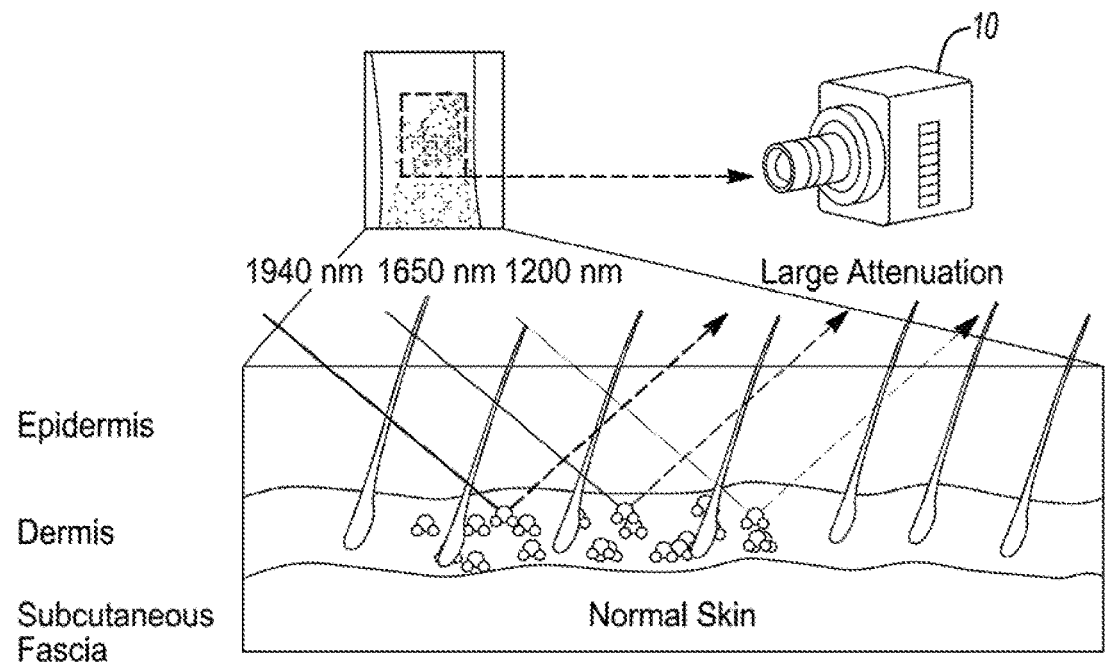
FIG. 1B illustrates diagrammatically the reflectance of Short Wave Infrared (SWIR) in viable skin that is well hydrated (top) and in burned skin (bottom). The increased water content increases attenuation of the reflectance at the sample measured wavelengths of 1940 nm 1650 nm and 1200 nm.
Figure 1B:
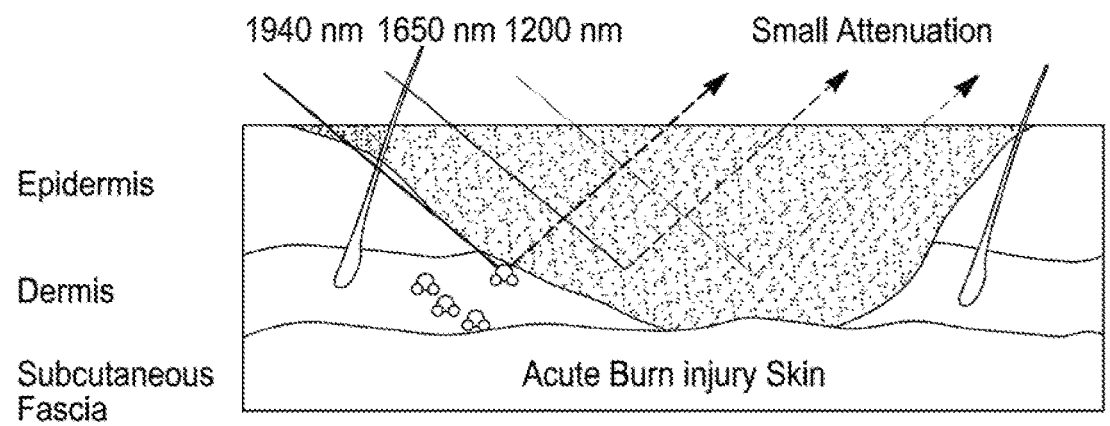
Figure 1C:
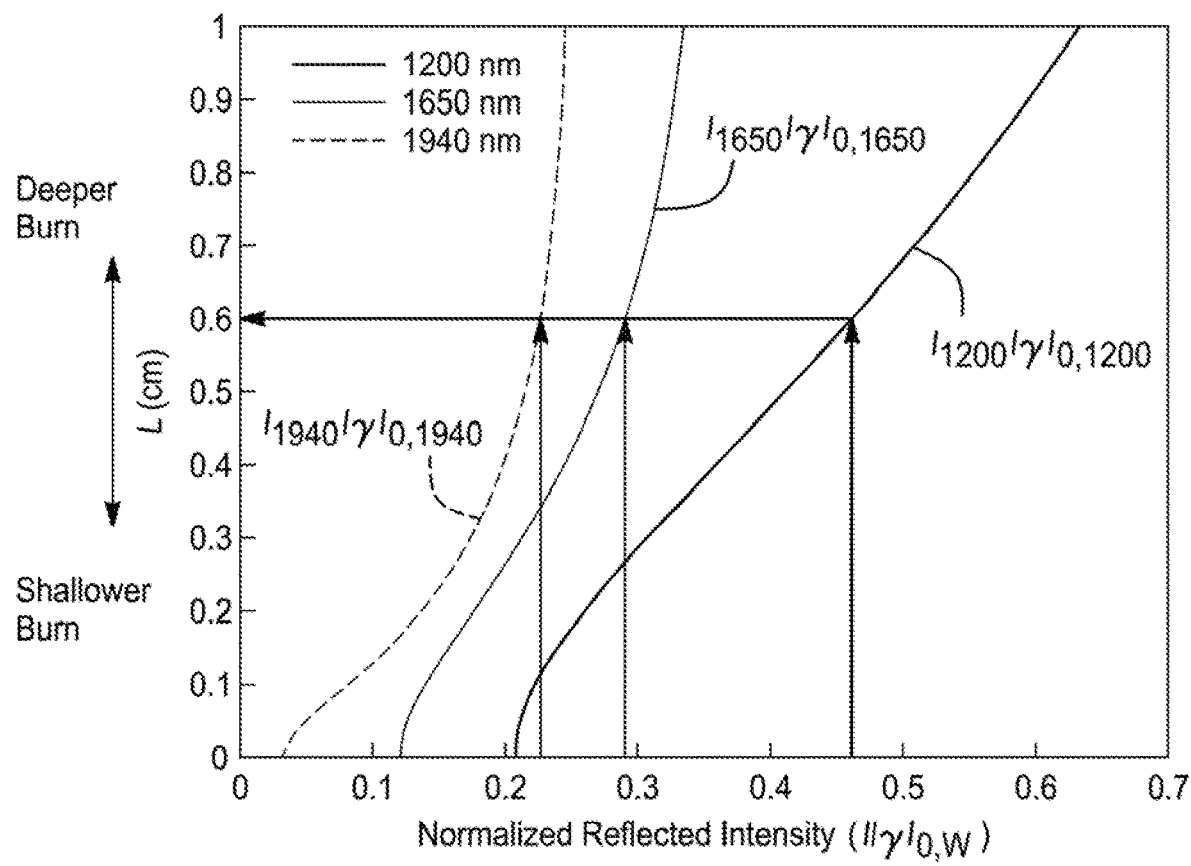
FIG. 1C illustrates previous findings that demonstrated the correlation between depth of injury and normalized reflected intensity, which was both strongest and most specific at 1940 nm.

Results from SWIR system 10 correlated with the depth of injury, as delineated by histology, was obtained. In superficial burns, there was minor injury to the epidermis, and the dermis remained intact. SWIR system 10 demonstrated more reflectance attenuation in these regions compared to those areas that were more deeply burned (that is, the deeper is the burn, the more light is reflected—see FIGS. 1C, 3B and 4A). In the setting of a deeper burn, both the epidermis and dermis were injured, as indicated by diffuse inflammation, subcutaneous edema, and disorganization of the dermal and epidermal architecture. Areas devoid of moisture based on imaging from SWIR system 10 were characterized by a greater depth of injury, as characterized by H&E stains, greater Caspace-3, and decreased Ki-67 stain. Therefore, SWIR system 10 accurately predicts tissue viability and depth of thermal injury.

Analytical model for Depth of burn versus light intensity.

According to the present teachings, an approximated model for the skin that includes dry (non-vital) and wet (vital) tissue layers (as seen in FIG. 5) provides a framework for calculating parameters to characterize the depth of a burn from the skin-air surface. The tissue is characterized by specific absorption coefficients for each SWIR wavelength; for all of the wavelengths the absorption of the wet layers is larger than the absorption in the dry layers as illustrated in Table 1 where we specify the values of those coefficients as determined from Bashkatov et al. (A. N. Bashkatov et al. 2005 J. Phys. D: Appl. Phys. 38 2543).

TABLE 1

| Wavelength (nm) | Without water (1/cm) | With water (1/cm) |
|---|---|---|
| 1200 | 0.5 | 2.4 |
| 1650 | 1.4 | 4.1 |
| 1940 | 2.0 | 15 |

In the SWIR range, the scattering in the skin is much less dependent of wavelength and water content as compared to absorption; the reduced scattering coefficient is about 15±5 l/cm in the 1000-2000 nm range. Therefore, one can factor the scattering out of the reflectance to define the intensity density light l detected by SWIR system 10 of the burned skin as:

$$I = \frac{I_0 \gamma}{2} \left( \frac{1 - e^{-\mu_1 2L}}{\mu_1} + \frac{e^{-\mu_2 2L}}{\mu_2} \right) \quad (1)$$

where $I_0$ is the incident light, $\gamma$ is the scattering factor, $\mu_1$ and $\mu_2$ are the absorption coefficients of the dry and wet tissue layers respectively ($\mu_2 > \mu_1$), and L is the distance between the air-skin interface and the dry-wet layers interface (i.e., L is the depth of the dead layers in the burnt skin, see FIG. 5).

The expression for the light intensity dependency on L depends on the absorption coefficients that are different for dry and wet tissue as well as for the different wavelengths of the light (see Table 1). In FIG. 6 we implement the absorption coefficients values of Table 1 in Equation 1 and the value of L is plotted as a function of the normalized reflected intensity at the 3 wavelengths set forth herein. It can be appreciated from the 3 traces in FIG. 6 that the deeper the burn, the monotonically higher is the reflected SWIR light intensity.

Use of multiple wavelengths in the NIR/SWIR regions.

In addition to the 1900-1950 nm region (nominally 1940 nm), in one embodiment, the present teachings employ other wavelengths, 1200 nm (scattering, lipids+collagen/proteins) and 1650 nm (collagen/proteins). In some embodiments, multiple wavelengths can be used to create an average value of burn depth for added accuracy. In some embodiments, the 1200 nm and/or 1650 nm wavelength may be used to correct for scattering because at that wavelength scattering is almost uniform across wavelengths. In some embodiments, 1450 nm wavelength can be used to measure water, with correction for lipids and proteins from other wavelengths. Because it has lower water absorbance, 1450 nm and 1940 nm together can provide depth profiling.

Combined Visible and NIR/SWIR Imaging

In some embodiments, a combined system having both visible 24 and NIR/SWIR imaging 12 can be used. In this way, as illustrated in FIG. 7, a Cassegrain (all-mirror) lens configuration can be used. Visible range camera can be mounted on the concave (front) mirror. Necessary electronic connections can follow supporting struts. In some embodiments, a similar arrangement can be used employing a catadioptric (refractive lens+curved mirror) configuration.

In some embodiments, a conventional cold mirror (reflecting wavelengths below about 700 nm) could be used. In such embodiments, readily available visible range video cameras, including cell phone cameras, can be used. The positions can be interchanged and a hot mirror used.

In some embodiments, side-by-side cameras can be used. In such embodiments, software and/or hardware solutions may be necessary to correct for the different angles. In some embodiments, the SWIR/NIR camera can point directly at the region of interest, while the visible light camera is at a more oblique angle. The reason is that the axis distortion required to correct for the angle also removes some of the image. A visible light camera with 5-15 megapixels is inexpensive, but the more expensive SWIR camera has only 256×320=81,920 pixels.

Visible NIR/SWIR Illumination

In some embodiments, illumination setup is dictated by the imaging requirements and is balanced with the desire to maintain as compact configuration. FIG. 8 shows a diagram of a uni-directional light source that is best fit to match the Cassegrain imaging shown in FIG. 7. The illumination setup is placed in the outer surface of a cylinder whose symmetry axis is the optical axis of the visible and SWIR camera 12 as well as the mirrors and focusing lenses. Thus, an optimal uniform (shadow-less) illumination is achieved at minimal space of light sources.

In some embodiments, electronic control of the light sources can be provided. In some embodiments, multi-spectral imaging will be based on LEDs with different wavelengths distributed on the inner surface of a cylinder as shown in FIG. 8. The LEDs of different wavelengths will be switched on in sequence controlled by a switching control board and synchronized with the frames obtained with the SWIR camera 12. FIG. 9 illustrates the time protocol for switching a system with 4 distinct LED arrays. Each LED type is powered for a period of $\frac{1}{350}$ sec (the SWIR camera 12 frame rate=350 frames/sec) in sequence to complete a duty cycle that can be repeated for averaged imaging or improved signal-to-noise ratio (up to about 3 duty cycles per image to avoid strong motion artifacts).

4) Software:

The reflected light traces, as seen in FIG. 6, are consistent with FIGS. 10 and 11, showing that in animal and human skin, deep burns reflect more light than the healthy skin or superficial burns. Therefore, Equation 1 can be used to estimate the depth of the burn in the following steps:

(i) A one-time calibration image can be obtained by placing an SWIR mirror (for example, the optical diffuse reflectors WS-1 or WS-1-SL from Ocean Optics) in front of the camera at a distance comparable to the distance between the camera and the skin. That image can be used to generate a 2-dimensional image of the incidence light density at each of the 3 different wavelengths, which are expected to have small heterogeneities.

(ii) Three images of partial thickness (superficial), full thickness (deep) burned skin patches as well as normal, reference, skin patches can be taken at the 3 wavelengths in sequence.

(iii) The scattering factor $\gamma$ can be determined using the incident and reflected light at the reference normal skin areas, where it is known that $L \approx 0$ as the epidermis thickness is about 100 μm only by $\gamma = 2I\mu_2/I_0$ (see Equation 1).

(iv) Each reflection image can be normalized to the incidence image $I_0$ and the scattering factor $\gamma$ at the corresponding wavelength.

(v) The resulted normalized values of the reflected light can be then mapped into the burn depth L through the traces shown in FIG. 6 for each wavelength. Each wavelength provides an independent value of L and therefore they can be averaged for enhanced reliability.

Display of Information

In some embodiments, as illustrated in FIG. 10, the imaged data can be displayed on a computer monitor or other device. Information from the NIR/SWIR images is overlaid on a visible light image of the burn region to provide detailed boundary information. Thus, the surgeon has direct information of where the deep and partial thickness burned tissue is, superimposed on what he/she actually sees. The overlay could be a false color image in a contrasting color such as yellow or green, or outlined regions of tissue to be debrided. An overlaid image need not be solid—it may be partially transparent or it may be hatched, dotted, or otherwise easily seen over the visible light image.

In some embodiments, as illustrated in FIG. 11, the imaged data can be displayed and/or projected directly upon the tissue using a burn boundary, areas of interest, or other markers, projector system 26. This permits direct visualization of the necessary debridement areas.

Conclusions

Objective measures of burn wound depth are important to improve physicians' ability to properly diagnose and treat burn injuries and tissue damage. The present teachings represent a robust non-invasive technology that can be used by care givers (both expert and non-expert in spectroscopy or even in burns) to distinguish between superficial and deep burns to determine which wounds may benefit from surgical debridement. In a porcine model, there is a clear dichotomy between SWIR metrics in superficial burns versus deep burns.

The benefit of measurement in the short wave infrared spectrum (1000-2000 nm) lies in the ability to penetrate into deeper tissues than with light in the mid-infrared or visible spectrum (400-700 nm). Additionally, the presence of O—H and C—O sensitive wavelengths within the SWIR region allows detection of compounds such as collagen or lipid, and water with greater sensitivity compared to NIR or other modalities. Moisture levels, a tissue quality commonly evaluated by burn surgeons to gauge the depth of tissue injury, are best captured in the short wave infrared spectrum, with signal intensity at 1940 nm being 260 times greater than at 970 nm. Accordingly, SWIR system 10 is able to detect differences in moisture and reliably differentiate superficial from deeper burns in a non-invasive fashion using an in vivo porcine model with histology as the gold standard for comparison.

The results align with those of previous studies that indicate the benefit of SWIR technology. SWIR optical sensing of skin has been previously used to characterize porcine and human skin. However, these measurements have largely been performed ex-vivo and have not been used to assess burns or traumatic wounds. SWIR has also been used to identify atherosclerotic plaque and stages of malignancy in breast cancer. The non-invasive method of measuring the composition and nature of deeper anatomic structures is critically important to the overarching benefit of SWIR imaging. However, SWIR imaging has not been investigated in the past for to efficacy in the setting of thermal injury. SWIR imaging is currently used to quantify skin moisture after application of topical facial cosmetics. For burn injuries specifically, although technologies have been developed to facilitate wound care and management, these modalities including LDI, ICG video angiography, and NIR imaging all have important limitations that have restricted the potential for standardized clinical use in military, veteran, and civilian populations.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A short-wave infrared (SWIR) imaging system for assessing a tissue damage depth, the SWIR imaging system comprising:
   a light source for illuminating a wound or burn area, the light source having a plurality of light producing devices operated at a plurality of different wavelengths in a range of 1000 nm and 2500 nm;
   a light registering camera system in a still or movie format in the SWIR range being within 1000 nm and 2500 nm, the light registering camera system configured to image the wound or burn using the light source at the plurality of different wavelengths and output multi-spectral reflectance imaging information containing reflectance intensity information;
   wherein the light registering camera system comprises a plurality of SWIR filters;
   and
   a detection system configured to receive the multi-spectral reflectance imaging information containing the reflectance intensity information and process the multi-spectral reflectance imaging information to determine a tissue damage depth at a dry-wet layers interface based on specific absorption coefficients of each of the plurality of different wavelengths, the detection system configured to correct for scattering and create an average value of the tissue damage depth using at least two of the plurality of different wavelengths and output a signal in response to the determined tissue damage depth;
   a projector system receiving the assessment from the detection system and visibly projecting information upon the wound or burn;
   wherein the projected information is wound or burn boundary information, area of interest, or debridement information.

2. The SWIR imaging system according to claim 1 wherein the plurality of SWIR filters comprises a 1200±10 nm filter, a 1650±10 nm filter, and a 1940±10 nm filter.

3. The SWIR imaging system according to claim 1 wherein the detection system averages the imaging information and outputs a de-noised and normalized image.

4. The SWIR imaging system according to claim 1, further comprising:
   a mobile structure supporting the light source and the light registering camera system in a predetermined orientation, the mobile structure being portable.

5. The SWIR imaging system according to claim 1 wherein the detection system detects area of diffuse inflammation in a dermal or epidermal architecture.

6. The SWIR imaging system according to claim 1 wherein the detection system detects area of subcutaneous edema in a dermal or epidermal architecture.

7. The SWIR imaging system according to claim 1 wherein the detection system detects area of disorganization in a dermal or epidermal architecture.

* * * * *